United States Patent
Horvath et al.

(10) Patent No.: US 11,648,219 B2
(45) Date of Patent: May 16, 2023

(54) NON-CRYSTALLIZING CANNABIDIOL BLENDS

(71) Applicant: CHEMTOR, LP, Lockhart, TX (US)

(72) Inventors: Andrew Horvath, New Braunfels, TX (US); Scott Davis, Smithville, TX (US); Matthew Moore, Austin, TX (US); Josh Eldridge, Wichita, KS (US); James Hook, Austin, TX (US); William Lanier, Lake Placid, FL (US)

(73) Assignee: CHEMTOR, LP, Lockhart, TX (US)

( * ) Notice: Subject to any disclaimer, the term of this patent is extended or adjusted under 35 U.S.C. 154(b) by 0 days.

(21) Appl. No.: 17/158,392

(22) Filed: Jan. 26, 2021

(65) Prior Publication Data

US 2021/0228513 A1 Jul. 29, 2021

Related U.S. Application Data

(60) Provisional application No. 62/966,333, filed on Jan. 27, 2020.

(51) Int. Cl.
| | |
|---|---|
| *A01N 43/00* | (2006.01) |
| *A01N 43/46* | (2006.01) |
| *A61K 31/55* | (2006.01) |
| *A61K 31/192* | (2006.01) |
| *A61K 31/05* | (2006.01) |
| *A61K 9/00* | (2006.01) |

(52) U.S. Cl.
CPC ............ *A61K 31/192* (2013.01); *A61K 9/006* (2013.01); *A61K 9/0031* (2013.01); *A61K 9/0053* (2013.01); *A61K 9/0078* (2013.01); *A61K 31/05* (2013.01)

(58) Field of Classification Search
None
See application file for complete search history.

(56) References Cited

U.S. PATENT DOCUMENTS

| | | | |
|---|---|---|---|
| 9,376,367 | B2 | 6/2016 | Herkenroth et al. |
| 10,351,498 | B2 | 7/2019 | Mona et al. |
| 10,378,020 | B2 | 8/2019 | Sayre et al. |
| 2014/0221469 | A1 | 8/2014 | Ross et al. |
| 2016/0228385 | A1 | 8/2016 | Sievers et al. |
| 2017/0008870 | A1 | 1/2017 | Dibble et al. |
| 2019/0382807 | A1 | 12/2019 | Sayre et al. |

FOREIGN PATENT DOCUMENTS

| | | | | |
|---|---|---|---|---|
| WO | WO-2016127111 A1 | * | 8/2016 | ............ A61K 31/05 |
| WO | WO 2019/056123 A1 | | 3/2019 | |

OTHER PUBLICATIONS

International Search Report and Written Opinion issued by the United States Patent and Trademark Office as International Searching Authority for International Application No. PCT/US21/15074 dated Apr. 28, 2021. (10 pages).

* cited by examiner

*Primary Examiner* — Layla Soroush
(74) *Attorney, Agent, or Firm* — Haynes and Boone, LLP

(57) ABSTRACT

A non-crystallizing blend includes cannabidiol (CBD) and cannabidiolic acid (CBDA). A method of forming a non-crystallizing blend of CBD and CBDA includes obtaining a CBD isolate including at least 80% by weight CBD, obtaining a CBDA isolate including at least 80% by weight CBDA, and combining and mixing the CBD isolate and the CBDA. A method of treating a condition includes administering a therapeutically effective amount of a non-crystallizing blend of CBD and CBDA to a patient in need thereof.

5 Claims, No Drawings

NON-CRYSTALLIZING CANNABIDIOL BLENDS

CROSS-REFERENCE TO RELATED APPLICATIONS

The present application claims the benefit of U.S. Provisional Application No. 62/966,333, filed Jan. 27, 2020, the disclosure of which is incorporated herein by reference in its entirety.

TECHNICAL FIELD

The present disclosure is related to cannabinoid blends. More particularly, this disclosure is related to compositions containing cannabidiol (CBD) and cannabidiolic acid (CBDA) that do not crystallize.

BACKGROUND

Cannabinoids occur in the hemp plant *Cannabis sativa* primarily in the form of cannabinoid carboxylic acids (referred to herein as "cannabinoid acids"). "Neutral cannabinoids" are derived by decarboxylation of their corresponding cannabinoid acids. The more abundant forms of neutral cannabinoids include tetrahydrocannabinol (THC), cannabidiol (CBD), cannabichromene (CBC), and cannabigerol (CBG).

Of present interest is CBD and its corresponding cannabinoid acid, cannabidiolic acid (CBDA). For reference, the decarboxylation of CBDA to form cannabidiol (CBD) is illustrated below:

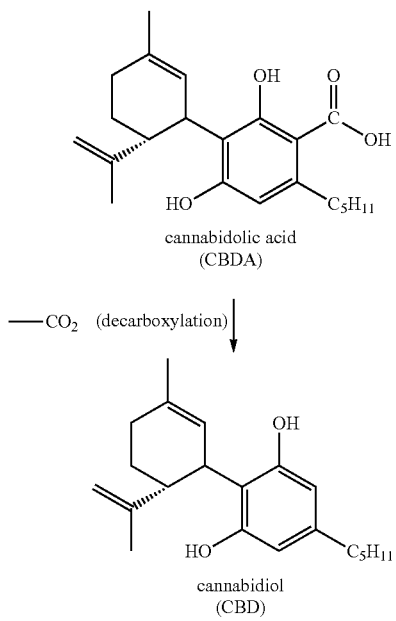

CBD has been shown to have therapeutic effects and may be used to treat, as examples, chronic pain, anxiety, inflammation, and/or seizures. As such, highly concentrated CBD compositions are desirable in order to maximize such therapeutic effects. Unfortunately, highly concentrated CBD has a tendency to crystallize, wherein the crystalline form is difficult or impossible to administer by preferred methods, such as vaporizing, applying topically, or consuming via sublingual drops. When crystallization does occur, remedial efforts, such as heating the CBD, may temporarily return the CBD to non-crystalline form. However, such remediation is inconvenient and, if not done correctly, potentially dangerous.

Using low concentration CBD compositions may reduce or eliminate unwanted crystallization. However, the therapeutic effects of such compositions are diminished, requiring greater consumption to achieve similar effects as compared with a highly concentrated CBD composition. Moreover, many of the carriers used to dilute the CBD have unknown and/or harmful effects when ingested or inhaled (via pyrolysis). For instance, polyethylene glycol (PEG) and other glycols may decompose to formaldehyde when exposed to hot vaporizing devices.

Accordingly, there remains a need for a highly concentrated CBD product that does not crystallize.

BRIEF SUMMARY

The present disclosure provides highly concentrated CBD that may be maintained in non-crystalline form by the addition of CBDA. The present disclosure also provides methods for preparing blends of CBD and CBDA, such methods including obtaining concentrated CBD and concentrated CBDA and mixing these components in controlled proportions. Methods of administering the blend include oral ingestion, inhalation of vapor, and absorption through topical application or sublingual or buccal administration.

DETAILED DESCRIPTION

The following descriptions are provided to explain and illustrate embodiments of the present disclosure. The described examples and embodiments should not be construed to limit the present disclosure.

Blend of CBD and CBDA

The present disclosure provides a non-crystallizing blend containing at least CBD and CBDA. As used herein, unless otherwise noted, the term "non-crystallizing" refers to a composition that does not form crystals at standard ambient temperature and pressure (i.e., 25° C. and 1 atm). A "non-crystallizing" composition may include microcrystals (less than 100 microns in length) and/or nanocrystals. Similarly, formation of microcrystals and/or nanocrystals does not constitute "crystallization" as used herein.

The blend includes, as a primary component, CBD. According to some embodiments, the blend contains CBD in an amount of at least 50% by weight, at least 55% by weight, at least 60% by weight, at least 65% by weight, at least 70% by weight, at least 75% by weight, at least 80% by weight, at least 85% by weight, at least 90% by weight, at least 91% by weight, at least 92% by weight, at least 93% by weight, at least 94% by weight, at least 95% by weight, at least 96% by weight, at least 97% by weight, or at least 98% by weight based on a total weight of the blend. According to some embodiments, the blend contains CBD in an amount of at most 99% by weight, at most 97% by weight, at most 95% by weight, at most 92% by weight, at most 90% by weight, at most 87% by weight, at most 85% by weight, at most 82% by weight, at most 80% by weight, at most 78% by weight, at most 75% by weight, at most 70% by weight, at most 65% by weight, at most 60% by weight, or at most 55% by weight based on a total weight of the blend. According to some embodiments, the CBD is present in in the blend amount ranging between any logical combination of the above upper and lower limits.

The blend includes CBDA in an amount effective to disrupt crystallization of CBD. According to some embodiments, the blend contains CBDA in an amount of at least 0.5% by weight, at least 1% by weight, at least 2% by weight, at least 5% by weight, at least 7% by weight, at least 10% by weight, at least 12% by weight, at least 15% by weight, at least 18% by weight, at least 20% by weight, at least 25% by weight, at least 30% by weight, or at least 35% by weight, based on a total weight of the blend. According to some embodiments, the blend contains CBDA in an amount of at most 40% by weight, at most 35% by weight, at most 30% by weight, at most 25% by weight, at most 20% by weight, at most 17% by weight, at most 15% by weight, at most 12% by weight, at most 10% by weight, at most 7% by weight, at most 5% by weight, or at most 3% by weight based on a total weight of the blend. According to some embodiments, the CBDA is present in in the blend amount ranging between any logical combination of the above upper and lower limits.

According to some embodiments, the blend contains only CBD, CBDA, and inevitable impurities (less than 0.1% by weight impurities). According to some embodiments, the blend contains a total amount of CBD and CBDA of at least 50.5% by weight, at least 52% by weight, at least 55% by weight, at least 60% by weight, at least 65% by weight, at least 70% by weight, 75% by weight, at least 80% by weight, at least 85% by weight, at least 90% by weight, at least 95% by weight, at least 98% by weight, at least 99% by weight, at least 99.5% by weight, or at least 99.9% by weight based on a total weight of the blend.

According to some embodiments, a weight ratio of CBD to CBDA is from 1.25 to 100, from 2 to 75, from 2 to 50, from 2 to 40, from 2 to 30, from 2 to 20, from 2 to 10, from 2 to 8, from 2 to 5, from 3 to 50, from 3 to 40, from 3 to 30, from 3 to 20, from 3 to 10, from 3 to 8, from 3 to 6, from 4 to 50, from 4 to 40, from 4 to 30, from 4 to 20, from 4 to 10, from 4 to 8, from 5 to 50, from 5 to 40, from 5 to 30, from 5 to 20, or from 5 to 10.

In some embodiments, the blend does not crystallize at standard ambient temperature and pressure for at least 24 hours, at least 48 hours, at least 7 days, at least 14 days, at least 28 days, at least 56 days, at least 112 days, at least 168 days, or at least 1 year. In some embodiments, the blend does not crystallize within a temperature range of −30° C. to 50° C., −20° C. to 50° C., −10° C. to 50° C., 0° C. to 50° C., −30° C. to 40° C., −20° C. to 40° C., −10° C. to 40° C., 0° C. to 40° C., 0° C. to 30° C., 10° C. to 50° C., 10° C. to 40° C., 10° C. to 30° C., 20° C. to 40° C., or 20° C. to 30° C. at 1 atm. In some embodiments, the blend does not crystallize within any one of the foregoing temperature ranges for at least 24 hours, at least 48 hours, at least 7 days, at least 14 days, at least 28 days, at least 56 days, at least 112 days, at least 168 days, or at least 1 year.

In some embodiments, the CBD and CBDA form a eutectic system. The suppressed melting point of the system reduces or eliminates crystallization of the CBD and may also lead to increased solubility and bioavailability of the CBD.

Unless otherwise indicated, the blend is free of, or substantially free (less than 0.3% by weight) of psychoactive cannabinoids. In another embodiment, the blend contains psychoactive cannabinoids in an amount that does not provide a discernable psychoactive effect when administered to a subject.

The blend described herein may contain cannabinoids other than CBD and CBDA. The other cannabinoids include, but are not limited to, tetrahydrocannabinol (THC), cannabidivarin (CBDV), cannabichromene (CBC), cannabichromevarin (CBCV), cannabigerol (CBG), cannabigerovarin (CBGV), cannabielsoin (CBE), cannabicyclol (CBL), cannabivarin (CBV), cannabitriol (CBT), tetrahydrocannibivarin (THCV), cannabigerol monomethyl ether (CBGM), cannabichromenic acid (CBCA), tetrahydrocannabinolic acid (THCA), nabilone, and rimonabant. Additionally, analogs or derivatives of these cannabinoids can be used. In some embodiments, these other cannabinoids are present in the blend in a total amount of 10% by weight or less, 5% by weight or less, 3% by weight or less, 2% by weight or less, 1% by weight or less, 0.5% by weight or less, or 0.1% by weight of less based on a total weight of the blend.

In some embodiments, the blend includes other naturally occurring compounds found in *Cannabis sativa*, such as terpenes and terpenoids, sterols such as phytosterols, triglycerides, alkanes, squalenes, tocopherols, carotenoids, flavonoids, polyphenols, cannflavins, and alkaloids. In some embodiments, these other compounds are present in the blend in a total amount of 10% by weight or less, 5% by weight or less, 3% by weight or less, 2% by weight or less, 1% by weight or less, 0.5% by weight or less, or 0.1% by weight of less based on a total weight of the blend.

In any of the embodiments disclosed herein, the CBDA may be replaced, wholly or partially, by a CBDA salt such as a salt including sodium, potassium, magnesium, calcium, and other suitable monovalent and divalent salts for introduction to a human biophase. Suitable salts are also described in WO2019/056123, which is herein incorporated by reference in its entirety. As used herein, "salt" refers to acid or base salts of the compounds used in the blend of the present disclosure. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference. Those of skill in the art will appreciate that some of the foregoing salts may be more suitable for blends used for administration by absorption or ingestion rather than inhalation.

In any of the embodiments disclosed herein, the blends may include one or more additives. The additives may include an oil such as medium-chain triglycerides (MCT), olive oil, soybean oil, canola oil, cotton oil, palmolein, sunflower oil, corn oil, rapeseed oil, grape seeds oil, hemp oil, pomegranate oil, avocado oil, peppermint oil, tomato oil, isopropyl myristate, oleyl lactate, coco caprylocaprate, hexyl laurate, oleyl amine, oleic acid, oleyl alcohol, linoleic acid, linoleyl alcohol, ethyl oleate, hexane, heptanes, nonane, decane, dodecane, D-limonene, neem oil, lavender oil, peppermint oil, anise oil, rosemary oil, sage oil, hibiscus oil, berries oil (any type), menthol, capsaicin, grape seed oil, pumpkin oil, hemp oil and similar essential oils or triglycerides or esters of fatty acids and mixtures thereof. The additive may include diluents, anti-oxidants, buffers, bacteriostats, suspending agents, solubilizers, thickening agents, gelling agent, emollients, moisturizers, stabilizers, preservatives, buffers, coloring agents, a fragrance, aromatic agents, flavoring agents, flavor masking agents, absorbers, filters, electrolytes, proteins, and/or chelating agents. The stabilizer may include an acid stabilizer to prevent the CBDA from decarboxylating. In some embodiments, the additives are present in the blend in a total amount of 10% by weight or less, 5% by weight or less, 3% by weight or less, 2% by weight or less, 1% by weight or less, 0.5% by weight or less, or 0.1% by weight of less based on a total weight of the blend.

Method of Producing the Blend

The method for preparing the blend of CBD and CBDA is not particularly limited. The method generally includes steps of separately obtaining a CBD source and a CBDA source and mixing the CBD and CBDA. The final composition of the blend produced by the present method may be as described above.

The source of the CBD and CBDA is not particularly limited. In some embodiments, the CBD and/or CBDA may be isolated from plant material or cell cultures of *Cannabis sativa* or produced synthetically. Isolation and synthetic production of CBD and CBDA are discussed in U.S. Pat. Nos. 9,376,367 and 10,378,020 and U.S. Patent Application Publication No. 2019/0382807, which are each herein incorporated by reference in their entireties.

In some embodiments, the CBD source may be in a pure or nearly-pure (at least 99.5% pure) form. Alternatively, the CBD may be provided in a CBD-rich composition, containing, e.g., at least 80%, at least 85%, at least 90%, at least 95%, at least 98%, or at least 99% CBD by weight. The CBD-rich composition may contain one or more of the other cannabinoids and additives discussed above. The CBD-rich composition may additionally or alternatively include other naturally occurring compounds found in *Cannabis sativa*, as discussed above. In some embodiments, the CBD may be dissolved in a solvent, e.g., dimethyl sulfoxide, ethyl acetate, water, dimethylformamide, methanol, ethylene dichloride, chloroform, propanol, ethanol, isobutanol, formamide, methylene dichloride, butanol, isopropanol, tetrahydrofuran, dioxane, benzene, toluene, xylene, or combinations thereof. The method may include a step of removing the solvent before or after mixing the CBD and CDBA.

In some embodiments, the CBDA source may be in a pure or nearly-pure (at least 99.5% pure) form. Alternatively, the CBDA may be provided in a CBDA-rich composition, containing, e.g., at least 80%, at least 85%, at least 90%, at least 95%, at least 98%, or at least 99% CBDA by weight. The CBDA-rich composition may contain one or more of the other cannabinoids and additives discussed above. The CBDA-rich composition may additionally or alternatively include other naturally occurring compounds found in *Cannabis sativa*, as discussed above. In some embodiments, CBDA may be dissolved in a solvent, such as those discussed above. The method may include a step of removing the solvent before or after mixing the CBD and CDBA.

In some embodiments, the CBD source and the CBDA source are combined with a solvent, such as the solvent discussed above, prior to the mixing step. The solvent may be removed after the mixing step by, e.g., evaporation optionally under vacuum and/or heat.

In one or more embodiments, the method may further include obtaining a terpene-rich composition containing, e.g., at least 80%, at least 85%, at least 90%, at least 95%, at least 98%, or at least 99% of total terpenes by weight. The terpene-rich composition may include a single terpene or a blend of two or more terpenes. The method may include mixing the terpene-rich composition with the CBD source and the CBDA source, and optionally the solvent. In some embodiments, the terpene-rich composition may act as a solvent in the blend. Based on a total weight of the blend, the terpene-rich composition may constitute at most 45% by weight, at most 40% by weight, at most 35% by weight, at most 30% by weight, at most 25% by weight, at most 20% by weight, at most 15% by weight, or at most 10% by weight.

In any embodiment, the method may include a warming or heating step to facilitate mixture of the blend. In some embodiments, one or more steps of the method are performed under vacuum.

In some embodiments, the method may include adding one or more of the additives discussed herein in the amounts disclosed herein. In some embodiments, the method may include adding one or more of the other cannabinoids discussed herein in the amounts disclosed herein. In some embodiments, the method may include adding one or more of the other naturally occurring compounds found in *Cannabis sativa* discussed herein in the amounts disclosed herein.

In any embodiment, the blend produced by the method disclosed herein may be stored under controlled conditions. For instance, the blend may be stored at ambient temperature and pressure. In some embodiments, the blend may be stored under increased pressure, which may retard $CO_2$ evolution.

Administration of the Blend

The blends described herein may be administered in any practical manner. In some embodiments, the blend of CBD and CBDA may be vaporized and inhaled. Heating of CBDA facilitates decarboxylation to CBD. The decarboxylation of CBDA results in a loss of 13.3% by weight due (lost as $CO_2$ gas). As such, assuming complete decarboxylation of the CBDA upon vaporization, a blend consisting of, e.g., 25% by weight CBDA and 75% by weight CBD would have an effective CBD potential of 96.675% as compared with the initial weight of the blend. With lesser amounts of CBDA in the blend, the CBD potential is even greater.

In some embodiments, vaporization of the blend may be facilitated by a vaporizing device such as a vape pen, a vaporizer, a heating coil, or an aerosolizer. In some embodiments, the vaporizing device includes a heating element in order to facilitate decarboxylation. In some embodiments, the vaporizing device may employ a removable cartridge housing the blend. The cartridge may be sealed prior to installation in the vaporizing device and, in some embodiments, may be sealed under pressure. This pressure could retard the evolution of $CO_2$ from the CBDA. In any embodiment, the vaporizing device can include a power supply, which may be a portable power supply, such as a battery.

In some embodiments, the blend of CBD and CBDA may be orally ingested. Generally, ingestion does not result in as high of a CBD potential as compared with vaporization since the CBDA will not decarboxylate (or at least not to as high of a degree) absent heat. However, CBDA itself provides therapeutic effects when ingested. Alternatively, in some embodiments, the blend may be heated prior to ingestion in order to facilitate decarboxylation of the CBDA. For instance, the blend could be incorporated into a food item and cooked therewith to increase the CBD content.

In some embodiments, the blend of CBD and CBDA may be absorbed through topical application to the skin (transdermal application) or through sublingual or buccal administration. The absorption may be appropriately tailored for local delivery to treat a specific portion of the body or for systemic delivery.

In some embodiments, the blend may be administered in the form of a reservoir or hydrogel transdermal patch and may comprise one or more permeation enhancers including, but not limited to: dimethyl isosorbide; glyceryl monooleates; fatty acid alcohols such as oleic acid; transcutol and other modified PEGs; humectants such as povidones and crosspovidones (polyvinylpyrrolidone polymers); film formers; polyacrylate pressure sensitive adhesives; silicone pressure sensitive adhesives; styrene-isoprene-styrene block copolymer adhesives; other hot melt adhesives; gellifiers; and/or excipients. In any of the preceding embodiments, the blend may further include a solvent such as those discussed above. For instance, dimethyl sulfoxide is a non-toxic, polar aprotic solvent capable of enhancing membrane permeability.

In some embodiments, the blend may be administered in the form of a lotion, cream, or gel and may comprise a surfactant including, but not limited to: anionic surfactants such as alkyl sulfates, alkyl ether sulfates, alkyl sulphonates, alkaryl sulfonates, α-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates, alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids, and the alkali metal, alkaline earth metal, ammonium, amine, and triethanolamine salts thereof; cationic surfactants such as alkyl amines, alkyl imidazolines, ethoxylated amines, quaternary compounds, and quaternized esters; amphoteric surfactants such as amino acids (e.g., N-alkyl amino acids and N-acyl amino acids), betaines, sultaines, and alkyl amphocarboxylates; and/or non-ionic surfactants such as aliphatic ($C_6$-$C_{18}$) primary or secondary linear or branched chain acids, alcohols or phenols, alkyl ethoxylates, alkyl phenol alkoxylates (especially ethoxylates and mixed ethoxy/propoxy moieties), block alkylene oxide condensates of alkyl phenols, alkylene oxide condensates of alkanols, and ethylene oxide/propylene oxide block copolymers. In any of the preceding embodiments, the blend may further include a solvent such as those discussed above. For instance, dimethyl sulfoxide is a non-toxic, polar aprotic solvent capable of enhancing membrane permeability.

In embodiments employing sublingual or buccal administration, the blend may be provided, e.g., in a dropper bottle to facilitate accurate dosing. Generally, absorption of the present blend does not result in as high of a CBD potential as compared with vaporization or other methods that heat the blend. However, CBDA itself provides therapeutic effects when absorbed.

According to some embodiments, methods of treating a condition, such as pain, anxiety, inflammation, and/or seizures, include administering a blend of CBD and CBDA as described above by any of the above modes in a therapeutically effective amount to a subject in need thereof. In embodiments where the blend is heated before or during administration thereof, the therapeutically effective amount may be based on the CBD potential rather than the initial amount of CBD included in the blend. In embodiments not including heating, the therapeutically effective amount can be based on the amount of CBD included during preparation of the blend.

Modes of administration other than those described above may be employed as needed. For instance, the blend may be administered via colonic delivery. Colonic deliver may be suitable for treatment of Crohn's disease or other bowel inflammatory diseases. In such embodiments, water solubility of components in the blend may be advantageously increased in the intestinal tract (particularly, the colon) where pH values range from about 5 to about 8.

Although the present disclosure has been described using preferred embodiments and optional features, modification and variation of the embodiments herein disclosed can be foreseen by those skilled in the art, and such modifications and variations are considered to be within the scope of the present disclosure. It is also to be understood that the above description is intended to be illustrative and not restrictive. Many alternative embodiments will be apparent to those of in the art upon reviewing the above description. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the disclosure.

What is claimed is:

1. A non-crystallizing blend consisting of cannabidiol (CBD) and cannabidiolic acid (CBDA) and less than 0.1% by weight impurities;
    wherein the blend does not form crystals measuring greater than 100 microns for at least 24 hours at 25° C.

2. The blend according to claim 1, wherein the blend does not crystallize within a temperature range of 0° C. to 50° C.

3. A method of forming the non-crystallizing blend of claim 1, comprising:
    obtaining a CBD isolate consisting of CBD and less than 0.1% by weight impurities;
    obtaining a CBDA isolate consisting of CBDA and inevitable impurities; and
    combining and mixing the CBD isolate and the CBDA.

4. The method according to claim 3, further comprising mixing a solvent with the CBD isolate and the CBDA isolate,
    wherein the solvent is dimethyl sulfoxide, ethyl acetate, water, dimethylformamide, methanol, ethylene dichloride, chloroform, propanol, ethanol, isobutanol, formamide, methylene dichloride, butanol, isopropanol, tetrahydrofuran, dioxane, benzene, toluene, xylene, or combinations thereof; and
    removing the solvent.

5. The method according to claim 3, wherein the blend does not crystallize within a temperature range of 0° C. to 50° C.

* * * * *